United States Patent
Flynn et al.

(10) Patent No.: US 11,234,726 B2
(45) Date of Patent: Feb. 1, 2022

(54) BLADE POSITIONING DEVICE

(71) Applicant: GYRUS ACMI, INC., Southborough, MA (US)

(72) Inventors: John P. Flynn, Collierville, TN (US); Chee K. Teo, Cordova, TN (US); Kevin C. Edwards, Olive Branch, MS (US)

(73) Assignee: Gyrus Acmi. Inc., Westborough, MA (US)

( * ) Notice: Subject to any disclaimer, the term of this patent is extended or adjusted under 35 U.S.C. 154(b) by 771 days.

(21) Appl. No.: 15/153,040

(22) Filed: May 12, 2016

(65) Prior Publication Data

US 2016/0256189 A1    Sep. 8, 2016

Related U.S. Application Data

(63) Continuation of application No. 13/796,416, filed on Mar. 12, 2013, now Pat. No. 9,358,036.

(51) Int. Cl.
*A61B 17/3205*   (2006.01)
*A61B 17/32*   (2006.01)
(Continued)

(52) U.S. Cl.
CPC .... *A61B 17/3205* (2013.01); *A61B 17/32002* (2013.01); *A61B 17/1659* (2013.01);
(Continued)

(58) Field of Classification Search
CPC .......... A61B 17/32002; A61B 17/1659; A61B 2017/0046; A61B 2017/00477;
(Continued)

(56) References Cited

U.S. PATENT DOCUMENTS 2,211,216 A * 8/1940 Oster .................... B23B 31/202
                                                            15/23
3,223,088 A   12/1965 Barber et al.
(Continued)

FOREIGN PATENT DOCUMENTS

CN    104936539 A    9/2015
CN    104936539 B    5/2017
(Continued)

OTHER PUBLICATIONS

Robert Bosch Tool Corportion, DREMEL 75th Anniversary Rotary Tool Owner's Manual, 2007 (Year: 2007).*
(Continued)

*Primary Examiner* — Elizabeth Houston
*Assistant Examiner* — Michael G Mendoza
(74) *Attorney, Agent, or Firm* — Schwegman Lundberg & Woessner, P.A.

(57) ABSTRACT

A microdebrider comprising: (a) a handpiece; (b) an interchangeable tip connected to the handpiece; (c) an outer tune rotatably connected to the interchangeable tip, the outer tube including an outer tube window; (d) an inner tube extending at least partially through the outer tube, the inner tube including an inner tube window; (e) a lock selector connected to the inner tube; and (f) a bias device; wherein the bias device is movable, and upon movement of the bias device into contact with the lock selector the inner tube is immobilized so that the inner tube window is aligned with the outer tube window, aligned with a wall of the outer tube, or in a condition therebetween.

20 Claims, 4 Drawing Sheets

(51) Int. Cl.
*A61B 17/16* (2006.01)
*A61B 17/00* (2006.01)
*A61B 90/00* (2016.01)

(52) U.S. Cl.
CPC .............. *A61B 2017/00473* (2013.01); *A61B 2017/320004* (2013.01); *A61B 2017/320028* (2013.01); *A61B 2090/0811* (2016.02); *A61B 2090/08021* (2016.02)

(58) Field of Classification Search
CPC .... A61B 2017/320028; A61B 17/3205; A61B 2017/00473
See application file for complete search history.

(56) References Cited

U.S. PATENT DOCUMENTS

| | | |
|---|---|---|
| 3,955,284 A | 5/1976 | Balson |
| 4,014,342 A | 3/1977 | Staub et al. |
| 4,878,493 A | 11/1989 | Pasternak et al. |
| 5,112,299 A | 5/1992 | Pascaloff |
| 5,230,704 A | 7/1993 | Moberg et al. |
| 5,275,609 A | 1/1994 | Pingleton et al. |
| 5,352,222 A | 10/1994 | Rydell et al. |
| 5,376,078 A | 12/1994 | Dinger, III et al. |
| 5,395,312 A | 3/1995 | Desai |
| 5,405,348 A | 4/1995 | Anspach et al. |
| 5,413,556 A | 5/1995 | Whittingham |
| 5,480,389 A | 1/1996 | McWha et al. |
| 5,492,527 A | 2/1996 | Glowa et al. |
| 5,540,708 A | 7/1996 | Lim et al. |
| 5,560,373 A | 10/1996 | DeSantis |
| 5,569,254 A | 10/1996 | Carlson et al. |
| 5,609,573 A | 3/1997 | Sandock |
| 5,620,415 A | 4/1997 | Lucey et al. |
| 5,620,447 A | 4/1997 | Smith et al. |
| 5,712,543 A | 1/1998 | Sjostrom |
| 5,733,298 A | 3/1998 | Berman et al. |
| 5,792,167 A | 8/1998 | Kablik et al. |
| 5,810,809 A | 9/1998 | Rydell |
| 5,814,044 A | 9/1998 | Hooven |
| 5,849,023 A | 12/1998 | Mericle |
| 5,873,886 A | 2/1999 | Larsen et al. |
| 5,899,915 A | 5/1999 | Saadat |
| 5,904,681 A | 5/1999 | West, Jr. |
| 5,910,152 A | 6/1999 | Bays |
| 6,042,593 A | 3/2000 | Storz et al. |
| 6,053,923 A | 4/2000 | Veca et al. |
| 6,074,386 A | 6/2000 | Goble et al. |
| 6,152,941 A | 11/2000 | Himes et al. |
| 6,217,598 B1 | 4/2001 | Berman et al. |
| 6,221,088 B1 | 4/2001 | Bays |
| 6,246,638 B1 | 6/2001 | Zook et al. |
| 6,293,957 B1 | 9/2001 | Peters et al. |
| 6,296,638 B1 | 10/2001 | Davison et al. |
| 6,454,782 B1 | 9/2002 | Schwemberger |
| 6,494,892 B1 | 12/2002 | Ireland et al. |
| 6,716,215 B1 | 4/2004 | David et al. |
| 6,752,816 B2 | 6/2004 | Culp et al. |
| 6,824,550 B1 | 11/2004 | Noriega et al. |
| 6,979,332 B2 | 12/2005 | Adams |
| 7,150,747 B1* | 12/2006 | McDonald ........... A61B 18/148 606/45 |
| 7,179,255 B2 | 2/2007 | Lettice et al. |
| 7,237,990 B2 | 7/2007 | Deng |
| 7,247,161 B2 | 7/2007 | Johnston et al. |
| 7,276,074 B2 | 10/2007 | Adams et al. |
| 7,416,539 B2 | 8/2008 | Johnston et al. |
| 7,442,191 B2 | 10/2008 | Hovda et al. |
| 7,674,263 B2 | 3/2010 | Ryan |
| 8,109,956 B2 | 2/2012 | Shadeck |
| 8,202,288 B2 | 6/2012 | Adams et al. |
| 9,358,036 B2 | 6/2016 | Flynn et al. |
| 2001/0037114 A1 | 11/2001 | Dinger et al. |
| 2001/0047183 A1 | 11/2001 | Privitera et al. |

| | | |
|---|---|---|
| 2002/0038129 A1 | 3/2002 | Peters et al. |
| 2002/0165549 A1 | 11/2002 | Owusu-Akyaw et al. |
| 2003/0097129 A1 | 5/2003 | Davison et al. |
| 2003/0165794 A1 | 9/2003 | Matoba |
| 2004/0010258 A1 | 1/2004 | Carusillo et al. |
| 2004/0167427 A1 | 8/2004 | Quick et al. |
| 2004/0243163 A1 | 12/2004 | Casiano et al. |
| 2005/0159767 A1 | 7/2005 | Adams et al. |
| 2005/0222566 A1 | 10/2005 | Nahahira |
| 2005/0277970 A1* | 12/2005 | Norman ........... A61B 17/32002 606/180 |
| 2006/0259055 A1 | 11/2006 | Thorne et al. |
| 2007/0021752 A1 | 1/2007 | Rogers |
| 2009/0270896 A1 | 10/2009 | Sullivan et al. |
| 2010/0298763 A1 | 11/2010 | Adams et al. |
| 2010/0317998 A1 | 12/2010 | Hibner et al. |
| 2011/0009856 A1 | 1/2011 | Jorgensen et al. |
| 2011/0017801 A1 | 1/2011 | Zemlok et al. |
| 2011/0066142 A1 | 3/2011 | Tal et al. |
| 2011/0301578 A1 | 12/2011 | Muniz-Medina et al. |
| 2012/0221035 A1 | 2/2012 | Harvey |
| 2012/0191117 A1 | 7/2012 | Palmer et al. |
| 2012/0191119 A1 | 7/2012 | Hedstrom et al. |
| 2013/0004595 A1 | 1/2013 | Bhatia |
| 2014/0277036 A1 | 9/2014 | Flynn et al. |

FOREIGN PATENT DOCUMENTS

| | | |
|---|---|---|
| EP | 1201196 A1 | 5/2002 |
| EP | 2044893 A2 | 4/2009 |
| EP | 2133028 A2 | 12/2009 |
| EP | 2919675 A2 | 9/2015 |
| EP | 3097875 A1 | 11/2016 |
| GB | 2470607 A | 12/2010 |
| JP | 2016510624 A | 4/2016 |
| JP | 6064078 B2 | 12/2016 |
| WO | 96/37156 A1 | 11/1996 |
| WO | 97/23169 A1 | 7/1997 |
| WO | 98/38932 A1 | 9/1998 |
| WO | 2008/011308 A2 | 1/2008 |
| WO | WO-2014163666 A2 | 10/2014 |
| WO | WO-2014163666 A3 | 11/2014 |
| WO | WO-2014163666 A4 | 1/2015 |

OTHER PUBLICATIONS

Japanese Office Action for Application No. 2016-500100, dated Aug. 2, 2016.
PKS Cutting Forceps, General Surgery Products, Gyrus ACMI, An Olympus Company, available at www.gyrusacmi.com/user/display.cfm?display=product&pid=9063&catud=69&mainacat=General, last accessed and downloaded on Oct. 18, 2012.
Gyrus ACMI; Handpiece Cleaning and Maintenance Jun. 1, 2006.
Potentially Related Patent Application, U.S. Appl. No. 13/804,308, filed Mar. 14, 2013.
Potentially Related Patent Application, U.S. Appl. No. 13/803,380, filed Mar. 14, 2013.
Potentially Related Patent Application, U.S. Appl. No. 13/826,892, filed Mar. 14, 2013.
International Search Report, Application No. PCT/US2013/077758, filed on Dec. 26, 2013, dated Mar. 25, 2014.
People's Republic of China State Intellectual Property Office Action dated Sep. 26, 2016 for Application No. 201380070955.8.
Extended European Search Report for Application No. 16179122.3-1659, dated Oct. 20, 2016.
"U.S. Appl. No. 13/796,416, Non Final Office Action dated Oct. 21, 2015", 6 pgs.
"U.S. Appl. No. 13/796,416, Notice of Allowance dated Feb. 10, 2016", 7 pgs.
"U.S. Appl. No. 13/796,416, Preliminary Amendment filed Nov. 3, 2014", 4 pgs.
"U.S. Appl. No. 13/796,416, Response filed Jan. 11, 2016 to Non Final Office Action dated Oct. 21, 2015", 5 pgs.
"International Application Serial No. PCT/US2013/065199, International Preliminary Report on Patentability dated Sep. 24, 2015", 13 pgs.

(56) References Cited

OTHER PUBLICATIONS

"International Application Serial No. PCT/US2013/065199, International Search Report dated Oct. 10, 2014", 6 pgs.

"International Application Serial No. PCT/US2013/065199, Written Opinion dated Oct. 10, 2014", 11 pgs.

"European Application Serial No. 13783205.1, Communication under Rule 164(2)(a) EPC dated Dec. 17, 2015", 6 pgs.

"European Application Serial No. 13783205.1, Intention to Grant dated Apr. 8, 2016", 28 pgs.

"European Application Serial No. 13783205.1, Intention to Grant dated Jun. 10, 2016", 28 pgs.

"European Application Serial No. 13783205.1, Response filed Feb. 10, 2016 to Communication under Rule 164(2)(a) EPC dated Dec. 17, 2015", 6 pgs.

"European Application Serial No. 16179122.3, Communication Pursuant to Article 94(3) EPC dated Apr. 2, 2020", 5 pgs.

"European Application Serial No. 16179122.3, Response filed May 1, 2017 to Extended European Search Report dated Oct. 20, 2016", 3 pgs.

"Japanese Application Serial No. 2016-500100, Response filed Oct. 31, 2016 to Notice of Reasons for Rejection dated Aug. 2, 2016", 10 pgs.

"European Application Serial No. 16179122.3, Response filed Jul. 27, 2020 to Communication Pursuant to Article 94(3) EPC dated Apr. 2, 2020", 40 pgs.

\* cited by examiner

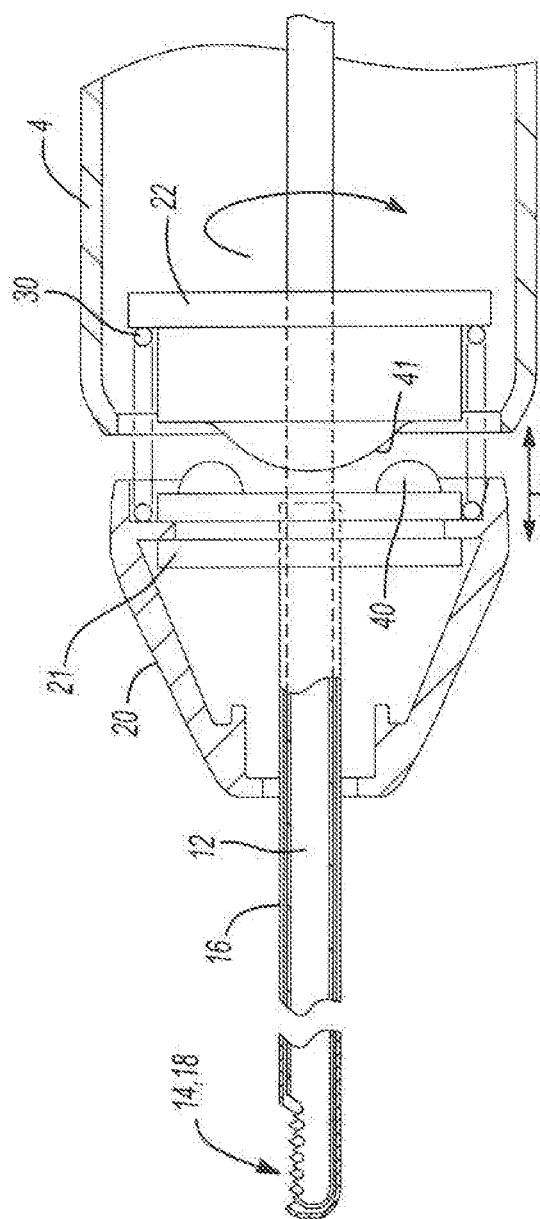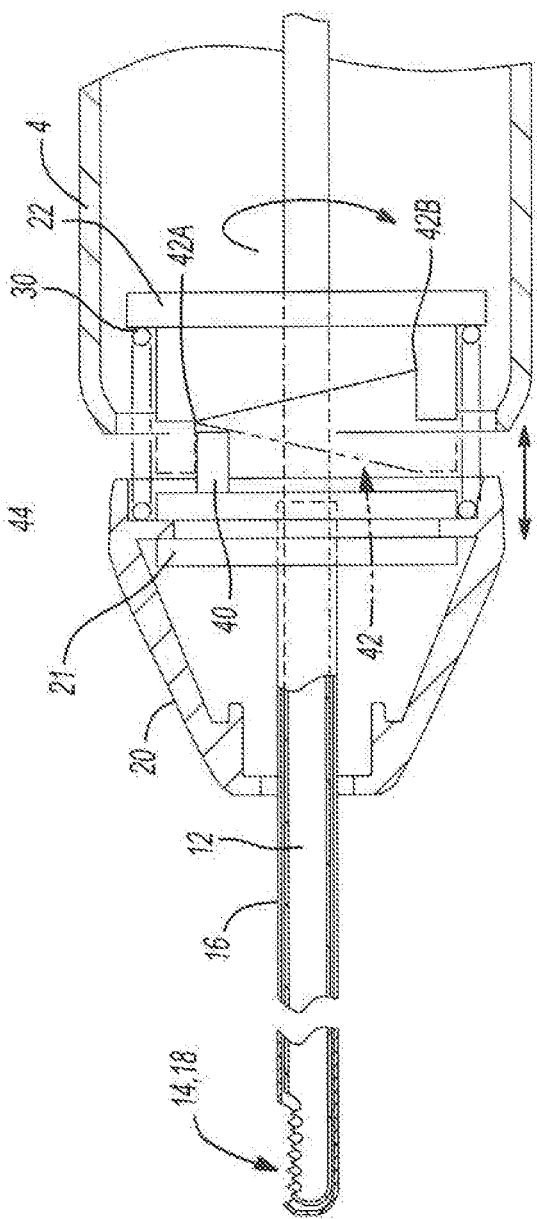

BLADE POSITIONING DEVICE

FIELD

The present teachings, generally relate to a debrider blade including two or more blades, and specifically a device for positioning a window of one blade relative to a window of an adjoining blade.

BACKGROUND

Generally debriders include a handpiece and a cutting portion. The handpiece includes a motor that rotates one or more blades in the cutting portion. The cutting portion includes a cutting window in an outer blade, and the cutting window exposes an internal cutting blade. The cutting blade includes a window with a sharp edge for performing a surgical technique such as removing tissue, cartilage, bone, or a combination thereof. The use of the cutting blade may result in bleeding and the cutting blade may include an energy source to coagulate blood, cauterize, or both, in order for the cutting blade to be used, the cutting blade is inserted into a patient and once a procedure is complete the cutting blade is removed from the patient. During insertion and subsequent removal of the cutting portion into and from a patient, the cutting portion may cause trauma the patient, thus, the user may try to orient the cutting blade so that the cutting blade does not align with the cutting window. In order for a user to align the cutting blade so that the cutting blade is covered by the outer blade the user may start and stop the blade until the blade is aligned as desired. This may require multiple attempts before the blades are aligned as desired and the blades may only partially be aligned as desired. The blades not being aligned as desired may result in an unnecessary cut in a patient. Further the user may desire to align the opening in the cutting portion with the opening in the outer blade so that the blades rosy be used for suction without cutting. When the cutting portion is located within a patient the user may not be able to determine the exact position of the cutting blade and aligning the openings for suction and/or removal may be more difficult as the user may not be able to visualize the position of the openings relative to each other. When more than two blades are present aligning the openings of all of the blades may be increasingly difficult for a user.

Examples of some devices that may be used to rotate a blade of a surgical instrument may be found in U.S. Pat. Nos. 3,223,088, 4,014,342; 5,112,299; 5,376,078, 5,492,527, 6,217,598; 7,276,074; and 8,202,288 and Patent Application Publication No. 2005/0277970; 2006/0259055 and 2012/0191117 all of which are incorporated by reference herein for all purposes, it would be attractive to have a device that accurately orients the openings of two or more tubes relative to each other it would be attractive to accurately orient the openings of two or more tubes while the tubes are covered. It would be attractive to have a device that locks the position of two or more tubes relative to each other so that the orientation of the tubes is fixed for insertion and/or removal. What is needed is a device to change the orientation of two or more tubes relative to each other without using a try and fail method. What is further needed is a device and method to orient the position of two bent tubes relative to each other without rotating a bent portion around an axis.

SUMMARY

The present teachings meet one or more of the present needs by providing, a microdebrider comprising: (a) a handpiece; (b) an interchangeable tip connected to the handpiece: (c) an outer tube rotatably connected to the interchangeable tip, the outer tube including an outer tube window; (d) an inner tube extending at least partially through the outer tube, the inner tube including an inner tube window; (e) a lock selector connected to the inner tube; and (f) a bias device; wherein the bias device is movable, and upon movement of the bias device into contact with the lock selector the inner tube is immobilized so that the inner tube window is aligned with the outer tube window, aligned with a wall of the outer tube, or a condition therebetween.

Another possible embodiment of the present teachings comprises: a microdebrider comprising, (a) a handpiece; (b) an interchangeable tip connected to the handpiece; (c) an outer tube rotatably connected to the interchangeable tip, the outer tube including an outer tube window; (d) an inner tube extending at least partially through the outer tube, the inner tube including an inner tube window; (e) an outer collet connected to the outer tube; (f) an inner collet connected to the inner tube; and (g) a bias member located between the inner collet and the outer collet; wherein the inner tube and the outer tube are immobilized when the inner collet and the outer collet are moved towards each other and into contact.

The teachings herein provide a device that accurately orients the openings of two or more tubes relative to each other. The teachings herein provide a device to accurately orient the openings of two or more tubes while the tubes are covered. The teachings provide a device that locks the position of two or more tubes relative to each other so that the orientation of the tubes is fixed for insertion and/or removal. The teachings provide a device to change the orientation of two or more tubes relative to each other without using a try and fail method. The teachings provide a device and method to orient the position of two bent tubes relative to each other without rotating a bent portion around an axis.

BRIEF DESCRIPTION OF THE DRAWINGS

FIG. 2 illustrates a cross-sectional view of another possible rotation device;

FIG. 3 illustrates a cross-sectional view of another example of a possible rotation device.

DETAILED DESCRIPTION

Figure 1A:
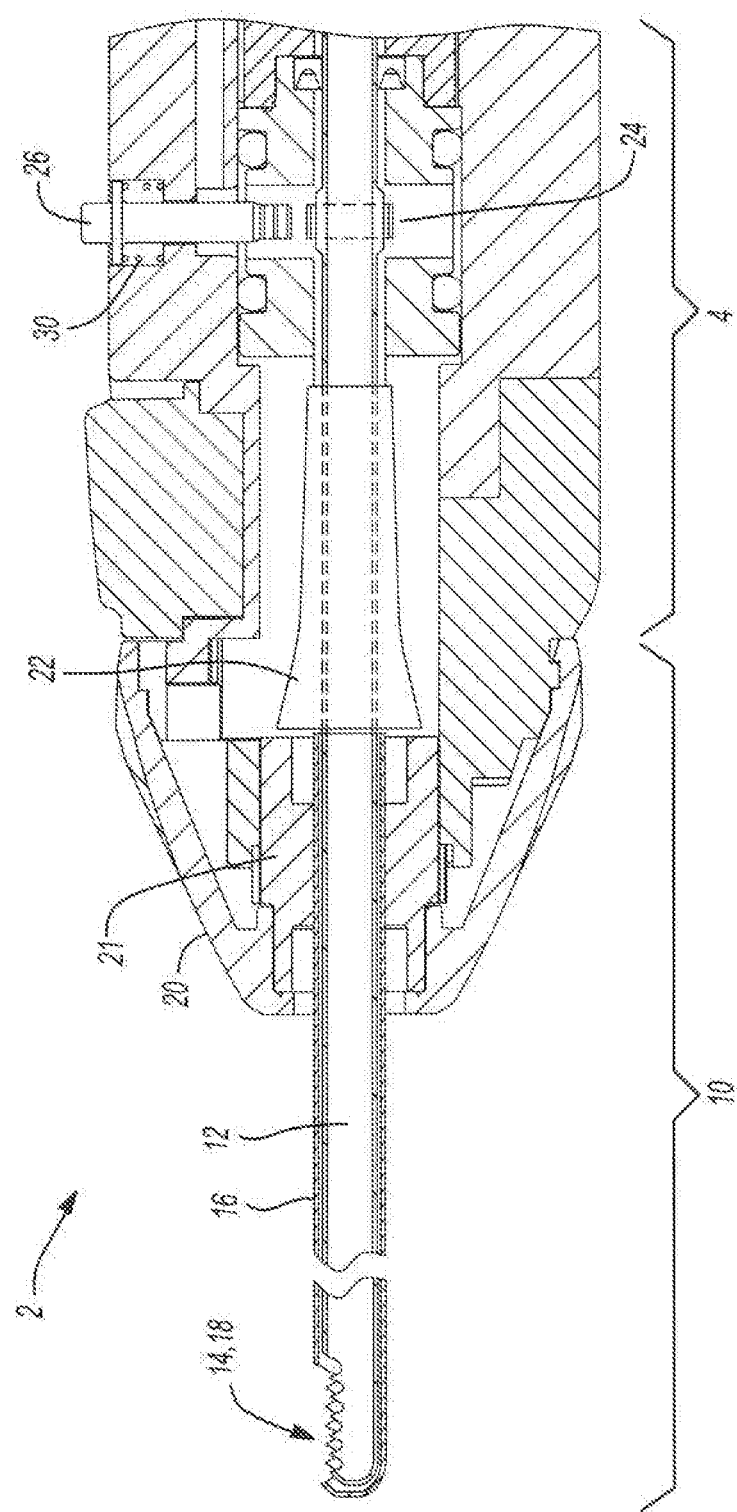
FIGS. 1A-1B illustrate a cross-sectional view of an one possible rotation device of the teachings herein.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The teachings herein provide a defender and preferably a microdebrider. The debrider generally includes a handpiece and a separable blade assembly. The handpiece includes an aperture that receives a portion of the blade assembly so that the handpiece may drive the blade assembly during use. The handpiece may include a motor and one or more gears that drive one or more rotary cutting tubes of the blade assembly. Other teachings of the handpiece may be gleaned from the teachings herein including those of paragraph Nos. 6-8, 26-45, 061-062, 065, and 70-72 and FIGS. 1-3 of U.S. Patent Application Ser. No. 61/731,919 filed on Nov. 30, 2012 teaching a handpiece and one or more connection portions for driving the separable blade assembly. The handpiece and blade assembly may be separable so that the handpiece, the blade assembly, or both may be cleaned, disposed of, or both after use. The handpiece, the blade assembly (e.g. an interchangeable tip), or both may include all or a portion of a positioning device.

The blade assembly includes a tip and a mechanical enclosure. The blade assembly (hereinafter interchangeable tip) includes a stylet (i.e., one or more tubes (e.g., inner tube, intermediate tube, outer tube, or a combination thereof)). Each of the inner tube, intermediate tube, and outer tube may include a window that exposes a portion of each respective tube, exposes a portion of each tube so that when rotated the exposed portions may be used for cutting, suction, or both. Each of the tubes may include a hole in addition to the window. Preferably, the hole is located in a distal end of the tubes so that when the windows are closed the hole may be used to remove fluids, debris, or both through the use of suction. The hole in the lube may be used for more precise suction and/or increased suction when the window in the inner tube, the intermediate tube, or both are closed. The blade assembly may include one or more tubes and preferably two or more tubes. The one or more tubes may be made of any biocompatible material. The one or more tubes may be made of a material that may be used to perform surgery. The one or more tubes may be made of any material that is sufficiently rigid to perform surgery, to be pushed, pulled, angled, or a combination thereof without bending, breaking; or both. The one or more tubes may be made of a material that conducts electricity. The one or more tubes may made of a polymer, metal, a natural material, a synthetic material, or a combination thereof. Preferably, the one or more tips are made of stainless steel or a surgical steel. Preferably, the stylet may include at least an outer tube and an inner tube. The stylet may include an inner tube and/or an intermediate tube at least partially disposed within the outer tube, and an inner tube at least partially disposed within the intermediate tube and the outer tube. Each of the two or more tubes may be connected. Preferably, each of the two or more tubes are axially independent of each other so that one or more of the tubes may rotate without rotating the other tubes. For example, an inner tube, an intermediate tube, or both may rotate inside of the outer tube. The one or more tubes may be straight, angled, bent, curved, flex-jointed (e.g., if the outer tube is bent then inner tube may be flexible to spin), or a combination thereof.

The one or more tubes may form one or more angles and the one or more angles may be any angle or combination of angles, include an angled portion, or both. The angled portion may be a rigid bend, an arcuate bend, a sweeping curve, or a combination thereof. The two or more tubes may include gearing to rotate the tubes. Preferably, the inner tube and/or intermediate tube includes a gear that is directly and/or indirectly connected to a motor so that the inner tube and/or intermediate tube is rotated. The gear may be in addition to a collet, a lock selector, or both that may also rotate the inner tube, the intermediate tube, or both. The ones or more tubes may extend from a blade module that includes a mechanical enclosure and forms an angle so that the one or more tubes may be used to perform a predetermined surgery or in a predetermined location.

The blade module may be any device that houses one or more moving parts of the disposable blade, a portion that one or more of the one or more blades extends through or both. The blade module may include a fixed portion that the user grips a rotatable portion, or both. The blade module may include a mechanical enclosure (i.e., an enclosure) that houses one or more moving parts, switches, controls, user inputs, or a combination thereof. The enclosure may be fixed relative to the nosecone, a collet, the handpiece, or a combination thereof. The enclosure may include one or more functional buttons. Preferably, the enclosure includes at least a control enclosure and a connection enclosure that each form a portion of the enclosure. The enclosure may include a seat that forms a movable connection, a pivotable connection, or both with a lock lever so that the lock lever may be moved between a locked position and an unlocked position so that the outer tube, the intermediate tube, the nosecone, or a combination thereof are prevented from rotating. Other teachings regarding the lock lever, components moved by the look lever (e.g., locking spline), a collet, nosecone. Internal gearing (e.g., pinion gears or nosepiece gears), a three tube system, or a combination thereof may be gleaned from the teachings herein, including those of Paragraph Nos. 005-007 and 0029-0054; and FIGS. 1-14 and related description in paragraph Nos. 0055-0070 of U.S. Patent Application Ser. No. 61/769,480, filed on Feb. 26, 2013, incorporated by reference herein for all purposes regarding a three tube system, a lock lever, components moved by the lock lever, the collet, the nosecone, and the internal gearing. Preferably, the lock lever is movably connected to the connection enclosure.

The connection enclosure may be any part of the interchangeable lip that connects the interchangeable tip to a power source so that power is supplied to the interchangeable tip. The connection enclosure may directly connect to the power source. Preferably, the connection enclosure directly connects to the handpiece and power is supplied to the interchangeable tip through the handpiece. The connection enclosure may be any part of the interchangeable tip that provides control signals to the handpiece, a generator, a control module, or s combination thereof. The connection enclosure may include one or more plugs that electrically connect the interchangeable tip to a handpiece, a power source, or both. Preferably, the one or more plugs include one or more connection pins so that power, signals (e.g., control signals, electrical signals, the like, or a combination thereof), or both are communicated between one or more components that are in electrical communication, signal communication, or both with the interchangeable tip. The connection enclosure may include one or more recesses, one or more connection supports, or a combination of both on each side for forming a fixed connection with a control enclosure.

The control enclosure may be any component that covers one or more functional components in the interchangeable tip. The control enclosure may be any component that allows a user to operate one or more functions of the interchangeable tip. Preferably, the control enclosure includes one or more control buttons, assists in actuating one or more buttons, or both that control all or a portion of one or more of the functional elements discussed herein. For example, the control enclosure may induce a bias device that may actuate and/or rotate one or more of the tubes. The control enclosure may enclose and protect all or a portion of a circuit, internal components, switches, or a combination thereof. Preferably, the control enclosure may protect all or a portion of a circuit, internal components, one or more switches, one or more locking devices, one or more selection devices, or a combination thereof, while allowing a user to actuate the one or more switches, one or more of the bias devices, rotate one or more of the bias devices, or a combination thereof so that one or more functions may be operated. All or a portion of the control enclosure may be malleable, compressible, movable, or a combination thereof so that one or more control buttons, one or more bias devices, or both may be actuated, moved, and protected by the control enclosure. The control enclosure may include one or more of the positioning devices discussed herein for aligning one or more tube windows with another tube window, a wall of another tube, or both. The control enclosure and connection enclosure may be located adjacent to a nosecone for rotating one or more tubes and preferably for rotating the outer tube and/or intermediate tube. The control enclosure may include all or a portion or a positioning device.

A positioning device may be any device used to align a window in one or more tubes with a window in one or more adjacent tubes, with a wall one or more adjacent tubes, or both. The positioning device may be any device that may rotate one or more tubes, prevent rotation of one or more tubes, or both. The positioning device may lock one or more tubes in a predetermined position. The positioning device may be used to rotate one or more tubes toggle one or more tube, or both to a desired position, between two or more positions, or both. Preferably, the positioning device is moved into contact with a collet, a lock selector, or both during rotation, toggling, movement, or a combination thereof of the inner tube and/or intermediate tube, and is free of contact with the collet, lock selector, or both during normal operation so that the inner tube, the intermediate tube, or both are free to rotate. The positioning device may be partially located in an interchangeable tip, partially located in a hand piece, fully located in an interchangeable tip, fully located in a handpiece, or a combination thereof. Preferably, the entirety of the positioning device is located in an internal portion of the interchangeable tip, the handpiece, or both except for all or a portion of the bias device. The positioning device may be movable perpendicular to the longitudinal axis of the one or more tubes (i.e., vertically movable), axially movable along the longitudinal axis and/or rotational axis of the one or more tubes, may be rotatable around an axis of movement, or a combination thereof. The positioning device may be comprised of one or more of a nosecone, outer collet, inner collet, lock selector, bias device, one or more bias members, an inner tube lock, a locking portion, an actuation selector, a director, fingers, an inner collet detent, an outer collet detent, or a combination thereof.

The nosecone may be any device that is connected to one or more of tubes so that the nosecone may be used to rotate one or more of the tubes. The nosecone may be used to rotate an angled portion of the stylet so that the tip of the stylet is moved. For example, when an angled stylet is used, rotation of the nosecone may rotate all of the tubes of the stylet around a rotational axis (e.g., if the tip is rotated 180 degrees then a bend in the stylet may be rotated so that a tip points in a first direction and when rotated the tip points in a second direction that is 180 degrees from the first direction). Stated another way, the entire stylet may move, not just reorient a portion of the stylet such as a window. In another example, in a two tube system the nosecone may be used to rotate the outer tube independently around an inner tube. The nosecone may be any device that may lock one or more of the tubes so that the one or more tubes are prevented from rotating. The nosecone may be any device that may rotate an intermediate tube located between an outer tube and an inner tube while the outer tube is locked in place. The nosecone may be a gripping portion for a user during use of the interchangeable tip. The nosecone may be fixed so that the nosecone may not be axially movable along the rotational axis of the inner tube; the intermediate tube, the outer tube, or a combination thereof; along a longitudinal axis of the stylet, or a combination of both. The nosecone may be axially movable along the rotational axis of the inner tube; the intermediate tube, the outer tube, or a combination thereof; along a longitudinal axis of the stylet; or a combination of both so that a position of each respective window may be locked in a desired position during insertion and/or removal of the stylet. For example, the nosecone may be axially moved in a proximal direction (i.e., towards the user) into a locking position and in a distal direction (i.e., away from the user) to release the look of the inner tube, the intermediate tube, or both. The nosecone may be located adjacent to an outer collet, locked to an outer collet, provide a static moving point for an outer collet, or a combination thereof.

The outer collet may be any device that is connected to an outer tube, an intermediate tube, or both. The outer collet may be fixedly connected to an outer tube, and intermediate tube, or both so that when the outer collet is moved the outer tube, the intermediate tube, or both is moved. In a two tube system, the outer collet will be connected to an outer tube. In a three tube system, the outer collet may be connected to the outer tube, the intermediate tube, or both. The outer collet may be axially movable, rotationally movable, or both. The outer collet may be connected to one or more devices that are external to the intermediate tube, the inner tube, or both so that the outer collet may be used to move only the outer tube. The outer collet may be fixed so that one or more adjacent components when moved into contact with the outer collet may form a locked relationship with the outer collet so that the outer collet and the adjacent component are prevented from rotating independently of each other. Preferably, the outer collet is axially movable so that the outer collet is moved into contact with an adjacent, part and both the outer collet and the adjacent part are rotationally immobilized and/or prevented from rotating independently of each other. For example, the outer collet may be axially movable into an inner collet. The outer collet may include an outer collet detent that may form a fixed connection with a complementary detent on an adjacent component.

The outer collet detent may be any device on an outer collet that forms a connection With an adjacent component so that the outer collet, the adjacent component, an inner collet, or a combination thereof are prevented from moving relative to each other; a looked configuration between the outer collet, and the inner collet, the adjacent component, or both is formed, the outer collet is rotationally aligned; or a combination thereof. The outer collet detent may be a projection, a recess, or both formed on and/or in the outer collet. Preferably, the outer collet detent may be a sinusoidal piece that includes both a projecting portion and a recessed portion so that the outer collet has a wavelike configuration. The outer collet detent may have an undulating configuration, a planar wall with a peg extending from the planar wall, a keyed portion, a complementary portion, or a combination thereof. Preferably, the outer collet detent is shaped so that when moved into contact with an adjacent inner collet detent a fixed connection is formed.

The inner collet detent may be any device on the inner collet that forms connection with the outer collet so that the outer collet and the inner collet are at least temporarily fixed relative to each other, movable with each other, locked in place, rotationally positioned, or a combination thereof. Preferably, the inner collet detent is a complementary feature, a keyed feature, or both with the outer collet detent. The inner collet detent may be a projection, a recess, or both. The inner collet detent may be sinusoidal, wavelike, a planar wall with a peg, a planar wall with a recess, keyed to an adjacent component, complementary to an adjacent component, or a combination thereof. The recess may have walls that extend along the axis of rotation. Preferably, the walls of the recess are angled so that when the outer collet detent extends into the recess the outer collet detent is moved to an end and the inner tube window, intermediate tube window, or both are moved to a predetermined position. The inner collet detent may be located on and/or in the inner collet so that when the inner collet detent and the outer collet detent are connected the inner tube window is open relative to and/or substantially aligned with the intermediate tube window, the outer tube window, or both. The inner collet detent may be located on and/or in the inner collet so that when the inner collet detent and the outer collet detent are connected the inner tube window is closed relative to and/or substantially opposed with the intermediate tube window, the outer tube window, or both. The inner collet detent may be shaped so that when the outer tube detent contacts the inner tube detent the outer tube detent, the inner tube detent, or both are automatically biased to a specific position. Preferably, the inner collet detent is located on and/or integrated into the inner collet so that the inner collet is movable and/or immobilized relative to the outer collet.

The inner collet detent may be any device on an inner collet that is fixedly connected to the inner tube. The inner collet may assist is moving the inner tube. The inner collet may drive the inner tube during use. Preferably, a gear drives the inner tube during use and the inner collet is used to orient tube when the inner tube is not powered, not in use, or both. The inner collet may rotate the inner tube around a rotational axis, may axially move the inner tube along the rotational axis, or both. The inner collet may be movable with the inner tube (i.e., another device such as a gear and/or lock selector may move the inner tube and the inner collet may be connected so that the inner collet moves with the inner tube). The inner collet may form a fixed connection with an outer collet. The inner collet may be free of contact with a bias member. Preferably, a bias member is located between the inner collet and the outer collet.

The bias member may be any device that may move one or more parts of the positioning device. The bias member may axially move the inner collet, the outer collet, or both relative to each other. The bias member may move an actuation selector, a bias device, or both. Preferably, the bias member moves the pieces of the positioning device from a locked position to a home position once a user releases the positioning device. The bias member may produce a force against a portion of the bias device; a housing of the interchangeable tip, the handpiece, or both; an inner collet, an outer collet a nosecone, or a combination thereof. The bias member may be any device that is elastically deformable, produces an expansion force, resists compression, or a combination thereof. The bias member may be rubber, a spring steel, a gasket, a spring, a deformable plastic, or a combination thereof. Preferably, the bias member is a spring that is in contact with the inner collet, the outer collet, a wall of the interchangeable tip, the bias device, or a combination thereof.

The bias device may be any movable device. The bias device may be any device that may be actuated from an external portion of a debrider so that rotation of an inner tube, an intermediate tube, or both may foe prevented. The bias device may be located m and/or extend through the interchangeable tip, the handpiece, or a combination of both. The bias device may be moved towards and/or away from an internal component of a debrider so that an inner tube may be immobilized, moved, or both. The bias device may be used to toggle between a window open position, a window closed position, or both. The bias device may be axially movable along the longitudinal axis of the debrider, moveable perpendicular to the longitudinal axis, rotationally around an axis of the bias device, or a combination thereof. For example, a bias device may be depressed and rotated around an axis so that while depressed the bias device may be used to rotate the inner tube window, the intermediate tube window, or both so that the inner tube window, the intermediate tube window, or both may be oriented relative to the window in the outer tube, a wall of the outer tube, or both. Preferably, the bias device and associated parts are movable so that during operation of the debrider the bias device is free of contact and the inner tube. Intermediate tube, or both are free to rotate without interference. More preferably, the bias device is movable so that during insertion, retraction, suction, or a combination thereof, the orientation of the inner tube window, intermediate tube window, or both is adjustable to a predetermined position and when insertion, retraction, suction, or a combination thereof is complete the bias device and associated parts move to a home position that is free of interference with normal operation of the defender. The bias device may be s button, the nosecone, a raised piece, or a combination thereof. The bias device may have any size, shape, and configuration so that the bias device may be used to look and/or bias a tube. The bias device may have a complementary shape to an adjacent device such as a lock selector. The bias device may include gears, teeth, a worm gear, a helical gear, or a combination thereof so that the bias device may be used to rotate the lock selector. The bias device may be made of any material that, may be sufficiently rigid to prevent a tube from rotating, to rotate a tube, or both. Preferably, the bias device is sufficiently rigid to prevent a tube from rotating, but not so rigid as to prevent the motor from rotating the tube and damaging the motor. The bias device may be a natural material, a synthetic material, a polymer, a metal, plastic, nylon, or a combination thereof. The bias device may be fixedly connected, removably connected, or both to a lock selector. The bias device may be located at any angle relative to the lock selector so that the bias device prevents rotation of the lock selector, the bias device may rotate the lock selector, or both. The bias device and lock selector may be substantially perpendicular to each other. For example, when viewed at a cross sectional view the bias device and lock selector may form substantially a right angle. The bias device and lock selector may be located relative to each other so that a movable connection is formed when the bias device is moved into contact with the look selector.

The look selector may be any device that may be connected to one or more of the tubes and may be contacted by the bias device so that the one or more tube are immobilized, biased by the bias device, or both. The lock selector may be rotatably connected to the inner tube, the intermediate tube, or both so that when the bias device is in the home position the lock selector rotates with the inner tube, the intermediate tube, or both. The lock selector may prevent rotation of the inner tube, the intermediate tube, or both when the lock selector is contacted by the bias device. Preferably, the look selector is free to rotate during operation of the debrider and is locked by a bias device during insertion, retraction, suction, or a combination thereof. The lock selector may be locked m any position so that a window of the tube may be locked in any rotational position (i.e., looked at any position in the 360 degrees of rotation). The lock selector may have predetermined locking positions (e.g., window oriented with another window, window oriented facing a wall, or both). The lock selector may rotate the tube when the bias device and the lock selector are connected. For example, the lock selector may include teeth that correspond with teeth in the bias device and upon rotation of the bias device the look selector and tube may be rotated. The lock selector may be any size, shape, and configuration so that the lock selector locks the position of a tube. The lock selector may be a gear, a worm gear, a helical gear, bow tie shaped, diamond shaped, two or more diamonds connected together, circular with recesses, oval with recesses, circular with projections, oval with projections, include a thinner center region, include tapered end regions, or a combination thereof. The lock selector may have a complementary shape to the bias device. The lock selector may have a shape so that when contacted by a portion of the bias device the lock selector is moved into a predetermined position. The lock selector may include one or more devices that move the lock selector to a predetermined position. The lock selector may include one or more lock selector directors.

The one or more lock selector directors may be any device that contacts a portion of the bias device and moves the lock selector towards a predetermined position, into a predetermined position, or both. The one or more lock selector directors may direct the lock selector to a locking position. The one or more lock selector directors may prevent the lock selector from being stopped in a non-locking position and then subsequently moving into a lock position so that the tube moves during insertion and/or removal. The lock selector directors may be blunt pointed, angled, rounded, steep, flat, or a combination thereof so that the lock selector director assists in directing the lock selector towards a predetermined position. The one or more lock selector directors may be located anywhere on the lock selector so that the lock selector is moved into a locking position. Preferably, the one or more lock selector directors may be located on the ends of the lock selector. The lock selector directors may direct a portion of the bias device towards a locking portion.

One or more locking portions may be any portion on the lock selector that forms a connection with the bias device that retains the inner tube, the intermediate tube, or both in a predetermined position, has a complementary fit with a portion of the bias device, or a combination thereof. The locking portion may be a recess, an indentation, a projection, or a combination thereof that locks the lock selector with the bias device. The locking portion may be located anywhere on the lock selector so that the lock selector is stopped at a predetermined location. The one or more locking portions may be located on the lock selector so that a window in the inner tube, the intermediate tube, or both are locked and aligned with, a window in the outer tube, the intermediate tube, or both. The one or more looking portions may be located on the lock selector so that a window in the inner tube, the intermediate tube, or both are locked and aligned with a wall of the outer tube, the intermediate tube, or both. The one or more locking portions may be located periodically around the lock selector. The one or more locking portions may be located every 60 degrees or more, every 75 degrees or more, or every 90 degrees or more. The locking portions may be located about 180 degrees from each other. The locking portions may be located so that an actuation selector may contact the locking portions, a region proximate to the locking portions, or both and retain the actuation selector in a position.

The actuation selector may be any part of the bias device that contacts a lock selector. The action selector may form a fixed connection with the look selector, move the lock selector, or both. The actuation selector may bias the lock, selector so that the actuation selector contacts a locking portion of the lock selector and retains the lock selector m place. The actuation selector may move the look selector so that the windows align or the window is aligned with a wall. The actuation selector may include one or more fingers that assist in moving the lock selector to a predetermined position.

The one or more fingers may be any device that assists in moving the lock selector to a predetermined position, assists in locking the lock selector in a position, or both. The one or more fingers may contact the lock selector at a locking portion, adjacent the locking portion, in an end region, in a central region, or a combination thereof. The actuation selector may include two or more fingers and preferably includes three fingers. During depression of the bias device one or more fingers may contact the lock selector and move the lock selector to a predetermined position. During the process of locking the lock selector one or more of the fingers may be free of contact with the lock selector. During a locking sequence one or more of the fingers may contact the lock selector. For example, during a locking sequence, the middle finger may first contact the lock selector and bias the lock selector to a first side or a second side using a director on the lock selector and a director on the finger. The lock selector may then next contact one of the outer fingers (e.g., a finger to the left and/or right of the middle finger). The lock selector upon contacting an outer finger may continue to rotate until all three fingers are in contact so that the lock selector and inner tube, outer tube, or both are immobilized. Any of the one or more fingers may include a director so that the fingers direct the lock selector to a predetermined location. Preferably, the middle finger includes a director.

The director may be any device on the actuation selector that is complementary to the lock selector direction so that the lock selector is directed to a predetermined locking position. The director may be any device that directs the took selector towards a lock position. The director may include any of the features of the lock selector director. Preferably, the director directs the lock selector to one side or the other so that the lock selector can be locked in place and the window may be locked in an open position or a closed position.

The window of the inner tube, the intermediate tube, or both may be locked in an open position a closed position or both. The intermediate tube window may be aligned with a wall of the outer tube thus closing the intermediate tube window so that the inner tube is not exposed and the inner tube may be located in any relationship. The intermediate tube window may be aligned with a window in the outer tube so that the inner tube is exposed. The inner tube window may be aligned with the intermediate tube window, the outer tube window, the inner tube wall, the outer tube wall, or a combination thereof. For example, the inner tube may not include a window and the inner tube may only have to be aligned with the intermediate tube window or the intermediate tube wall. The inner tube window may be aligned such that a user may leave the window open and use suction only or may close the window so that accidental cutting is prevented. The inner tube, intermediate tube, outer tube, nosecone, bias device, or a combination thereof may include one or more markings indicating the position of each relative window, the direction of bend of the stylet, or both.

The markings may be any marking that indicates the orientation of a window. The markings may rotate with the window so that the position of each window may be ascertained when the stylet is covered. The markings may indicate one or more predetermined positions, one or more locking positions, or both. The markings may be used by a user to perform a method of locking the windows.

The method may include one or more steps and the steps may be performed in virtually any order. The bias device may be moved from a home position to a lock position. The bias device may be rotated so that the window may be rotated. Two or more markings may be aligned. The bias device may be released. The inner tube window, intermediate tube window, outer tube window, or a combination thereof may be rotated. Two or more tubes may be aligned and suction may be applied. The tubes may be aligned and locked in an aligned position.

Figure 1B:
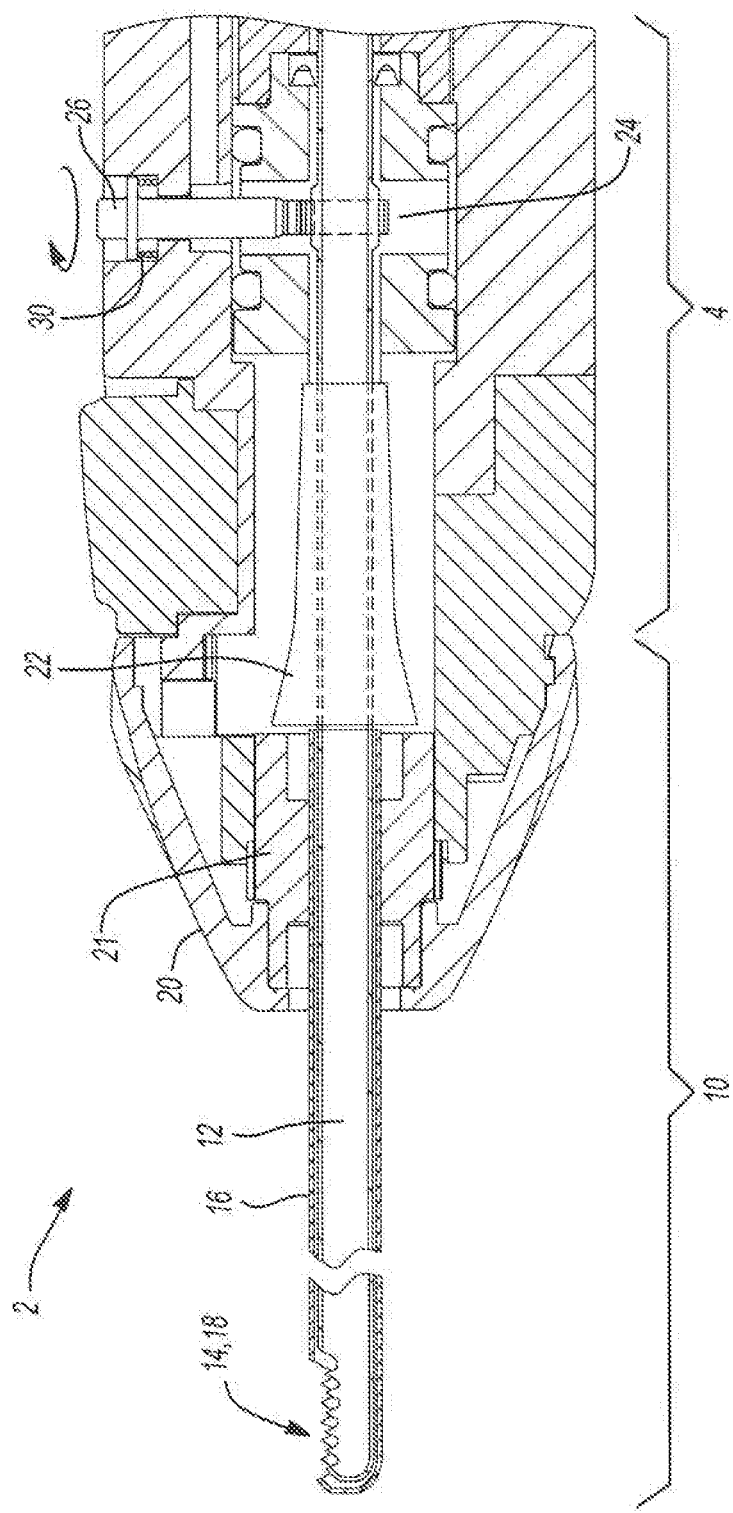

FIGS. 1A-1B illustrate a microdebrider 2 including a handpiece 4 and an interchangeable tip 10. The interchangeable tip 10 includes an inner tube 12 and an outer tube 16. The inner tube 12 includes an inner tube window 14 and the outer tube 16 includes an outer tube window 18. The outer tube 16 is connected to an outer collet 21, which is connected to and rotatable by a nosecone 20. The inner tube 12 is connected to and rotatable by an inner collet 22. As is illustrated in FIG. 1B the inner tube 12 is connected to a lock selector 24, and the bias device is depressed so that the bias device 26 and lock selector 24 are in communication. The bias device 26 can be rotated so that the bias device 26 rotates the lock selector 24, which rotate the inner tube window 14 so that the inner tube window 14 and the outer tube window 18 can be aligned, can be offset, or a combination thereof. As is illustrated in FIG. 1A, the bias device 26 is retracted away from the inner tube 12 by a bias member 30 that moves the bias device 26 to a home position. As illustrated in FIG. 1A, the inner tube 12 and lock selector 24 rotate without contacting the bias device 26.

FIG. 2 illustrates a cross-section view of a microdebrider. The microdebrider includes an outer tube 16 and an inner tube 12. The outer tube 16 is connected to an outer collet 21, which is connected to a nosecone 20 extending from the handpiece 4. The outer collet 21 is moved by a user along direction 44 towards and away from an inner collet 22 by pressing on and releasing the nosecone 20. The inner collet 22 is connected to an inner tube 12. The outer collet 21 includes an outer collet detent 40 that is moved into contact with an inner collet detent 41 on the inner collet 22 so that the position of the inner tube window 14 is movable and lockable in a fixed position relative to an outer tube window 18 (e.g., aligned with the outer tube window or offset with the outer tube window). A bias member 30 moves the outer collet 21 away from the inner collet 22 along the direction 44 so that the outer tube collet 21 returns to a home position one the nosecone 20 is released.

FIG. 3 illustrates a cross-sectional view of a microdebrider. The microdebrider includes an outer tube 16 with an outer tube window 18 and an inner tube 12 with an inner tube window 14. The outer tube 16 is connected to an outer collet 21 that includes an outer collet detent 40. The inner tube 16 is connected to an inner collet 22 including an inner collet detent 42. The inner collet detent 42 has a window open position 42A and a window closed position 42B so that upon movement of the inner collet 21 in the direction 44 the inner tube window 14 is locked in an open position or a closed position. The bias member 30 assists in separating the inner collet 22 and the outer collet 21 when a user releases the nosecone 20 so that the nosecone 20 moves away from the handpiece 4, and the inner collet 22 and the outer collet 21 return to a home position so that the inner tube 16 and the outer tube 12 are free to rotate independently.

Figure 4C:
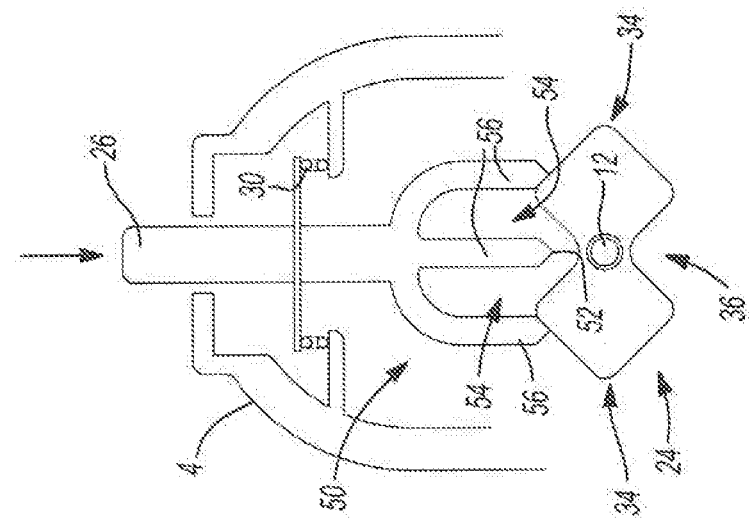
FIG. 4A-4C illustrate cross-sectional views of a selector device for rotating a tube.
Figure 4B:
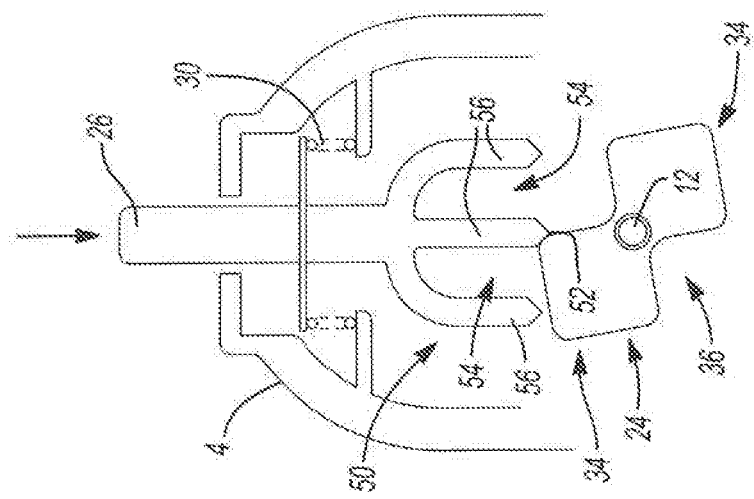
Figure 4A:
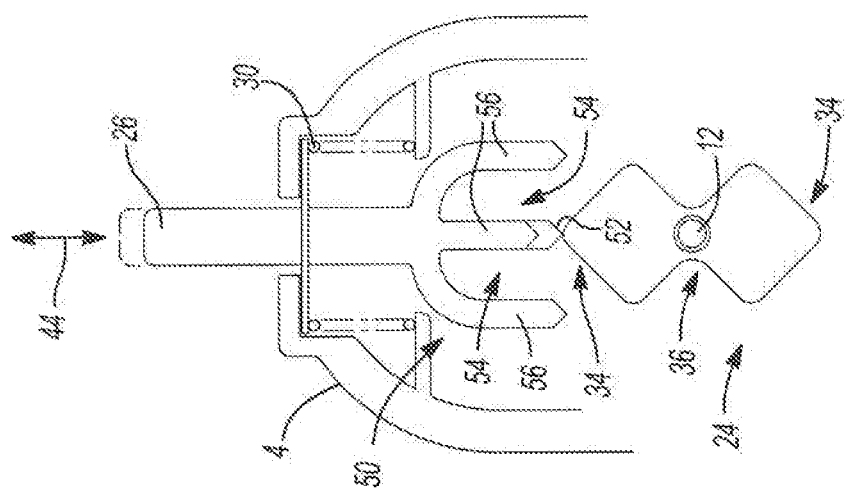

FIGS. 4A-4C illustrate a cross-sectional of a debrider during orientation and locking of the inner tube 12. The microdebrider includes a handpiece 4 having an inner tube 12. The inner tube 12 is connected to a lock selector 24. The lock selector 24 includes a lock selector director 34 and a locking portion 36. The handpiece 4 includes a bias device 26 that extends through the handpiece 4 so that a user can move the bias device in the direction 44. A bias member 30 is located between the handpiece 4 and the bias device 26 so that the bias member 30 moves the bias device 26 to a home position when a user releases the bias device 26. The bias device 26 includes an actuation selector 50 so that upon depression of the bias device 26, the bias device 26 is moved into contact with the lock selector 24 and the inner tube 12 is maintained in a position. The actuation selector 50 includes a director 52 that moves the lock selector director 34 to one side or the other of the director 52 (FIG. 4A to FIG. 4B) so that one or more fingers 56 of the actuation selector 50 contact the locking portion 36 of the lock selector 24 and immobilizes the inner tube 12 (FIG. 4C). The actuation selector 50 provides for movement of the inner tube 12 such that the window of the inner tube and the window of the outer tubs are aligned, offset, or in a condition therebetween.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A microdebrider comprising:
   a. a handpiece;
   b. an interchangeable tip connected to the handpiece, the interchangeable tip including:
      i. an outer collet;
      ii. an outer tube rotatably connected to the outer collet, the outer tube including an outer tube window located at a distal end of the outer tube;
      iii. an inner tube extending at least partially through the outer tube, the inner tube including an inner tube window located at a distal end of the inner tube;
   c. a lock selector connected to the inner tube; and
   d. a depressible and rotatable bias device extending radially outward from the inner tube along a longitudinal axis that intersects the lock selector, the bias device engageable with the lock selector and operable to rotate the lock selector;
   wherein depression of the bias device along the longitudinal axis causes engagement of the bias device with the lock selector, which in turn immobilizes the inner tube such that the inner tube window is aligned with the outer tube window, aligned with a wall of the outer tube, or in a condition therebetween; and
   wherein rotation of the bias device around the longitudinal axis causes rotation of the lock selector, which in turn rotates the inner tube window such that the inner tube window and the outer tube window are aligned with each other, offset from each other, or a combination thereof.

2. The microdebrider of claim 1, wherein the outer tube covers the inner tube window when the inner tube window and the outer tube window are offset from each other.

3. The microdebrider of claim 1, wherein the bias device is in communication with a bias member so that the bias member assists in retracting the bias device to a working position.

4. The microdebrider of claim 1, wherein the inner tube is connected to an inner collet, a gear, or both that assists in rotating the inner tube.

5. The microdebrider of claim 1, wherein the outer tube window is located distal of the outer collet.

6. The microdebrider of claim 5, wherein a user can rotate the outer tube by rotating the outer collet.

7. The microdebrider of claim 5, wherein the outer collet is a nosecone, the outer tube is directly connected to the outer collet.

8. The microdebrider of claim 1, wherein the lock selector has a window open position, a window closed position, or both.

9. The microdebrider of claim 1, wherein an intermediate tube is located between the inner tube and the outer tube.

10. A microdebrider comprising:
    a. a handpiece;
    b. an interchangeable tip connected to the handpiece, the interchangeable tip including:
       i. an outer tube rotatably connected to the interchangeable tip, the outer tube including an outer tube window;
       ii. an inner tube extending at least partially through the outer tube, the inner tube including an inner tube window;
       iii. an outer collet connected to the outer tube, the outer tube window is located distal of the outer collet;
       iv. an inner collet connected to the inner tube, the inner tube window is located distal of the inner collet;
    c. a depressible and rotatable bias device extending radially outward from the inner tube along a longitudinal axis; and
    d. a lock selector connected to the inner tube;
    wherein the outer tube is rotatably connected to the outer collet so that a user can rotate the outer tube by rotating the outer collet;
    wherein the outer collet is a nosecone;
    wherein the bias device is rotatably connected to the lock selector; and
    wherein depression of the bias device along the longitudinal axis causes engagement of the bias device with the lock selector and rotation of the bias device around the longitudinal axis causes rotation of the lock selector, which in turn rotates the inner tube window such that the inner tube window and the outer tube window are aligned with each other, offset from each other, or a combination thereof.

11. The microdebrider of claim 10, wherein upon movement of the bias device into contact with the lock selector the inner tube is immobilized so that the inner tube window is aligned with the outer tube window, aligned with a wall of the outer tube, or in a condition therebetween.

12. The microdebrider of claim 11, wherein the bias device is in communication with a bias member so that the bias member assists in biasing the bias device into contact with the lock selector.

13. The microdebrider of claim 11, wherein the bias device is in communication with a bias member so that the bias member assists in retracting the bias device to a working position.

14. The microdebrider of claim 10, wherein the outer tube covers the inner tube window when the inner tube window and the outer tube window are offset from each other.

15. The microdebrider of claim 10, further comprising a bias member for assisting in rotating the bias device.

16. The microdebrider of claim 10, wherein the inner tube is connected to a gear that assists in rotating the inner tube.

17. The microdebrider of claim 10, wherein an intermediate tube is located between the inner tube and the outer tube.

18. The microdebrider of claim 10, wherein the inner collet and the outer collet remain separate.

19. The microdebrider of claim 10, wherein the bias device includes a gear.

20. The microdebrider of claim 10, wherein the inner tube and the outer tube are coaxial.

* * * * *

UNITED STATES PATENT AND TRADEMARK OFFICE
CERTIFICATE OF CORRECTION

PATENT NO. : 11,234,726 B2
APPLICATION NO. : 15/153040
DATED : February 1, 2022
INVENTOR(S) : Flynn et al.

It is certified that error appears in the above-identified patent and that said Letters Patent is hereby corrected as shown below:

On the Title Page

In item (73), in "Assignee", in Column 1, Line 1, delete "Acmi." and insert --Acmi,-- therefor In Column 2, under "Other Publications", Line 1, delete "Corportion," and insert --Corporation,-- therefor Signed and Sealed this
Seventeenth Day of May, 2022

Katherine Kelly Vidal
*Director of the United States Patent and Trademark Office*